United States Patent
Roizen et al.

(10) Patent No.: US 6,497,658 B2
(45) Date of Patent: Dec. 24, 2002

(54) ALARM UPON DETECTION OF IMPENDING SLEEP STATE

(76) Inventors: Michael F. Roizen, 622 S. Woodlawn, Chicago, IL (US) 60637; Lawrence J. Gottlieb, 3837 Greenwood St., Skokie, IL (US) 60076; Avery Tung, 141 Sterling La., Wilmette, IL (US) 60091

(*) Notice: Subject to any disclaimer, the term of this patent is extended or adjusted under 35 U.S.C. 154(b) by 0 days.

(21) Appl. No.: 09/737,682

(22) Filed: Dec. 15, 2000

(65) Prior Publication Data

US 2001/0031930 A1 Oct. 18, 2001

Related U.S. Application Data

(60) Provisional application No. 60/172,569, filed on Dec. 17, 1999.

(51) Int. Cl.[7] .................................................. A61B 5/00
(52) U.S. Cl. ..................... 600/301; 600/544; 600/546; 600/300
(58) Field of Search ............................... 600/300, 301, 600/544, 546, 547; 340/575

(56) References Cited

U.S. PATENT DOCUMENTS

| | | | |
|---|---|---|---|
| 4,836,219 A | 6/1989 | Hobson et al. | 600/595 |
| 5,570,698 A | 11/1996 | Liang et al. | 600/558 |
| 5,813,993 A | 9/1998 | Kaplan et al. | 600/544 |
| 5,815,070 A | 9/1998 | Yoskikawa | 340/439 |
| 5,821,860 A | 10/1998 | Yokoyama et al. | 340/576 |
| 5,917,415 A | 6/1999 | Atlas | 340/575 |
| 5,999,846 A | 12/1999 | Pardey et al. | 600/544 |
| 6,011,991 A | 1/2000 | Mardirossian | 600/544 |

OTHER PUBLICATIONS

Ira J. Rampil, M.S., M.D., *A Primer for EEG Signals Processing in Anesthesia*, V. 89, No. 4, Oct. 1998 pp. 980–1002.
James W. Sleigh, John Andrzejowski, and Moiria Steyn-–Ross, *The Bispectral Index: A Measure of Depth of Sleep?*, Dec. 1999, pp. 659–661.
Ellen Leibenluft, Douglas E. Moul, Paul J. Schwartz, Pamela A. Madden, and Thomas a. Wehr, *A Clinical Trial of Sleep Deprivation in Combination With Antidepressant Medication*, May 1992, pp. 213–227.
Mary A. Carskadon and William C. Dement, *Normal Human Sleep: An Overview*, pp. 16–25.
"Monitor Adds Precision To Anesthesia" Robert Davis, Apr. 2000.
"What Does The Bispectral EEG Index Monitor?" European Journal of Anaesthesiology 2000, 17, 146–148.
"Johnson Controls Demonstrates New Technologies To Alert Drowsy Drivers" Jan. 2000.
"Development Of The Bispectral Index" Aspect Medical Systems.

*Primary Examiner*—Max Hindenburg
*Assistant Examiner*—Patricia Mallari
(74) *Attorney, Agent, or Firm*—Roberts Abokhair & Mardula, LLC

(57) ABSTRACT

The present invention monitors a physiological process intrinsic to humans and which measures directly the approach of a sleep state. When sleep onset is detected, the subject is restored to a fully awake state by an alert mechanism. Sleep onset is determined by monitoring EEG and EMG signals of the subject with a bispectral index monitor and applying an analysis algorithm to the index values output by the monitor. As a person tires, the value of their bispectral index begins to drop and then oscillate back and forth between two discrete levels. This pattern is consistent among various subjects and indicates an early warning of impending sleep, before a dangerous loss of vigilance has occurred.

22 Claims, 1 Drawing Sheet

ALARM UPON DETECTION OF IMPENDING SLEEP STATE

CROSS REFERENCE TO RELATED APPLICATIONS

This application claims priority under 35 U.S.C. § 119 (e) from provisional application no. 60/172,569, filed Dec. 17, 1999. The 60/172,569 provisional application is incorporated herein by reference, in its entirety, for all purposes.

BACKGROUND OF THE INVENTION

The present invention relates generally to the field of biofeedback. More particularly, the present invention relates to a device for detecting when a person is about to fall asleep and providing a feedback to the person indicating the impending sleep state.

Sleep deprivation is a common problem among airline pilots and other workers who are required to perform complex technical tasks over a prolonged period of time. Loss of sleep and fatigue in these settings can significantly impair cognitive function, and can lead to dangerous decrements in human performance. In particular, falling asleep at the controls of a commercial vehicle such as a truck, tanker, or airplane can lead to potentially catastrophic consequences. Besides the transportation context, drastic consequences may result by an operator falling asleep at the controls of a nuclear power plant, an electrical power grid, or other system that could impact many lives.

A number of proposals have been advanced to detect sleepiness by measuring various aspects of a subject's physiology or actions.

For example, headgear has been designed to measure eye and head movements. The resulting pattern of movements may then be correlated to sleep state, logged, and the log transmitted to a remote location. Unfortunately, detection of sleep onset based on changes in body movements is not a sufficiently timely method because the subject is likely quite inattentive by the time such sleep indications begin to occur. This method also requires sampling of the signal over a prolonged period of time, e.g., >30 seconds. This method. Is also subject to artifact if sleep onset is not associated with the anticipated eye and head movements. For further details, refer to U.S. Pat. No. 4,836,219, issued to Hobson, et al.

Automated monitoring of eye movement alone, as a surrogate for sleep, has also been proposed. It has the advantage of being a noninvasive monitor. However, it has a number of difficulties. In order to assess blink rate and eyelid speed, a normal baseline must be established. Thus, an extensive calibration time is required. Additionally, if a baseline is established during an already drowsy state, such a system may be unable to detect the relatively small change occurring with transition from drowsiness to sleep onset. Such a system is also susceptible to false positive measurements, because an increase in blink rate may not represent drowsiness, but rather dust in the eye or surprise. For further details, refer to U.S. Pat. No. 5,570,698, issued to Liang et al.

It has also been proposed to monitor a number of physiological changes at once and correlating them to drowsiness. Five parameters are described: pulse rate variability, vasomotor response, muscle tone, blood flow and reaction time. This method suffers from the disadvantage that there is no evidence firmly linking these physiological changes to sleep. For example, there may be several other explanations for change in vasomotor response. A high rate of false positive alarms is to be expected with this method. This method also requires baseline measurements that must be obtained over an extended period of time. This significantly limits the applicability of the method. As mentioned above, if the baseline is established during an already drowsy state, the small change from drowsiness to sleep may not be detectable. Additionally, physiological monitoring of sleep onset only detects the manifestations of sleep, and not the inattention that results from sleep onset. For further details, refer to U.S. Pat. No. 5,917,415, issued to Atlas.

A vehicle control device has been proposed that analyzes steering inputs and correlates these to the state of wakefulness of the operator. Specifically, measurements such as swerving movements (yaw rate), lateral movement, speed, and response time of the driver to these parameters are input to a computer, which sounds an alarm when values exceed certain preset parameters. For further details, refer to U.S. Pat. No. 5,815,070, issued to Yoshikawa. Similarly, it has been proposed to detect driver condition by comparison of driver inputs with previously defined baseline values. For further details, refer to U.S. Pat. No. 5,821,860 issued to Yokoyama et al. These more indirect methods suffer from most of the same problems note above with respect to methods that monitor head and eye movement and other physiological parameters. Of course, variations in both road and driver can lead to a highly variable baseline, and thus can only detect a case where the driver's condition is extremely degraded. These methods would require significant time to determine abnormal driving conditions, and may not detect degradation until too late to effectively arouse the driver.

Monitoring of EEG signals has also been proposed for monitoring wakefulness. The proposed device relies primarily on comparisons of driver response and road conditions. Such measurements are likely to be extremely variable from driver to driver and road to road, and false alarms are likely to be frequent. For further details, refer to Japanese Laid-Open Patent Publication (Kokai) no. 5-96971.

It has also been proposed to monitor EEG and use frequency analysis of the EEG to obtain "high frequency" (>30 Hz) components in order to predict sleep. This method suffers from a number of inaccuracies and disadvantages. Little data exists to firmly verify the hypothesis that EEG power in the high frequency range correlates reliably with drowsiness. No validation of this measure in explicitly sleep deprived humans has been provided. Moreover, it is unlikely that a continuous measure of drowsiness is available, as recent work suggests that drowsiness represents more an inability to maintain the waking state (i.e., propensity to enter the sleep state) than an ongoing alteration in waking brain function. Additionally, analysis of high frequency noise is technically difficult. Electrical noise, muscular movements (eyeblinks), etc. generate significant artifact. Accordingly, it is likely that false positives would be common. For further details, refer to U.S. Pat. No. 5,813,993, issued to Kaplan et al and Japanese Laid-Open Patent Publication (Kokai) no. 6-292661, by Mamoru et al.

Another proposal is to use a complex "neural network" to compare raw, unprocessed EEG signals to a known baseline signal to determine the probability of sleep. Such a device is proposed primarily for use as a portable sleep-scoring device, but may be adapted for use as a vigilance monitor. According to such a system, EEG signal is correlated to sleep stage, producing a "wakeogram." Such a correlation is based on human observation of the EEG, which has not clearly been correlated to loss of alertness. The proposed system requires a period of extensive prior calibration to train the processor. Such a need for prior calibration significantly reduces the applicability of their device. For further details, refer to U.S. Pat. No. 5,999,846, issued to Pardey et al.

Another system proposes monitoring of EEG signals, the transmission of those signals to a remote location. It does not, however, propose logging brain signals to a third party for data analysis. For further details, refer to U.S. Pat. No. 6,011,991, issued to Mardirssian.

Sleep onset is characterized by specific changes in the human electroencephalogram (EEG) and electromyelogram (EMG). Skilled operator analysis of such changes in the raw EEG can readily prevent humans from falling asleep, and has been used in clinical medicine to study the physiology of sleep states. For example, refer to Leibenluft, E., Moul, D. E., Schwartz, P. J., Madden, P. A., and Wehr, T. A., "A Clinical Trial of Sleep Deprivation in Combination With Antidepressant Medication" Psychiatry Research, 46(3): 213–27, March 1993 (93262082).

Automated devices based on computer interpretation of the raw EEG also exist. These devices, however, are large, unwieldy, and do not process the EEG in real time. Hence, they cannot be used to prevent inadvertent sleep.

Thus, what is needed is an automated device that processes and interprets EEG and/or EMG data in real time to detect sleep onset, without being unduly large. What is also needed is such a device that is further adapted to prevent sleep when sleep onset is detected. Such a device would be applicable to any situation where ongoing vigilance in the continuous performance of a difficult technical task is required. Such a device would also directly monitor the EEG, would detect the onset of sleep sooner than a device that monitors only response to stimuli.

SUMMARY OF THE INVENTION

It is an object of the present invention to provide a process that interprets EEG and/or EMG data in real time to detect sleep onset.

It is another object of the present invention to provide an automated device that processes and interprets EEG and/or EMG data in real time to detect sleep onset.

It is yet another object of the present invention to provide an automated device that processes and interprets EEG and/or EMG data in real time to detect sleep onset, and which is not unduly large.

It is still another object of the present invention to provide an automated device that processes and interprets EEG and/or EMG data in real time to detect sleep onset, and further to prevent sleep when sleep onset is detected.

It is a further object of the present invention to prevent a subject from sleeping by detecting sleep onset via processing and interpretation of EEG and/or EMG data in real time.

The present invention monitors a physiological process intrinsic to humans and which measures the sleep state directly.

Some of the above objects are obtained via a portable device capable of processing raw EEG in real time and transmitting a signal via auditory, vibrational, electrical, computer, global positioning device, or other means. This portable device prevents the inadvertent onset of sleep by sounding an audible alarm (or initiating other alert means) and awakening the subject when sleep was detected. Optionally, the portable device is empowered to automatically disengage machinery or automatically engage safety processes.

Because devices embodied according to the present invention are portable, they may be worn on the subject's person or mounted in the cabin of a vehicle being driven by the vehicle. Contact leads mounted on the subject enable recording of raw EEG data. The devices may be interchanged between plural vehicles. Another optional feature of the portable device is a transmitter to alert other remote devices via wireless communications.

When sleep onset was detected, the subject is awakened by an alert mechanism. The alert mechanism may be auditory, vibrational, electrical, light, RF, and may employ a global positioning system (GPS) device, and may be conducted via a network, or some combination of the foregoing.

Other of the above objects are obtained by using derived or transformed EEG and/or EMG signals to trigger an alarm system to prevent operators of potentially dangerous equipment from inadvertent sleep. This process uses a fixed or portable device that is capable of monitoring and interpreting the EEG and/or EMG in real time to determine when sleep onset is occurring. Upon detecting sleep onset, the process uses alerting apparatus that is capable of transmitting an alert signal via auditory, vibrational, electrical, light, RF, or some combination thereof. The alert signal may be conducted via a global positioning system (GPS) device, a network, or some combination thereof.

The present invention makes several advances over the prior art. First, a specialized EEG processing algorithm is used that goes beyond frequency spectral analysis to isolate high frequency components of the EEG, followed by "power," or amplitude analysis of those high frequency components. The present invention uses a higher order algorithm based in part on phase coupling of the different frequency components obtained from spectral analysis of the EEG signal. Such phase coupling is novel, undisclosed in the prior art and detects the general oscillatory coherence that occurs with sleep onset. This methodology is much more resistant to artifact, and represents an advance over other devices.

A number of feedback options are used to alert the wearer of the impending sleep state.

Furthermore, the present invention uses a processed measure of EEG activity based on real time analysis of the EEG signal. The processing algorithm targets the degree of phase coupling of the EEG, the degree of burst suppression, and the power ratio between different frequency bands, and can operate on a limited segment of EEG data. This is in stark contrast to prior art techniques that use only limited EEG processing, and require a more extensive segment of EEG data to accurately detect sleep stage. Further the processing algorithm of the present invention has validation as a measure of loss of alertness resulting from sleep onset. The processing of the present invention requires no calibration. Additionally, the processing algorithm is able to process out many sources of artifacts such as when sleep onset is not associated with anticipated eye and head movements.

The processing of the present invention relies not on body movement, but on EEG criteria. Because EEG defined sleep occurs prior to changes in body movements, the methods that rely upon body movements will not detect sleep onset rapidly enough. Further, the processing algorithm of the present invention does not require sampling of the signal over a prolonged period of time (e.g., 30 seconds) as in other devices.

The present invention measures sleep onset directly, and not by indirect actions of sleep on driver inputs. It is thus less susceptible to variability in driver and road conditions.

Moreover, the present invention does not require prior determination of "normal" behavior.

In addition, the present invention in an alternative embodiment transmits the signal to a remote location for analysis and subsequent alert to the operator.

Finally, the present invention relies upon EEG evidence of sleep that usually precedes behavioral manifestations of sleep.

BRIEF DESCRIPTION OF THE DRAWINGS

Additional objects and advantages of the present invention will be apparent in the following detailed description read in conjunction with the accompanying drawing figures.

DETAILED DESCRIPTION OF THE INVENTION

Figure 1:
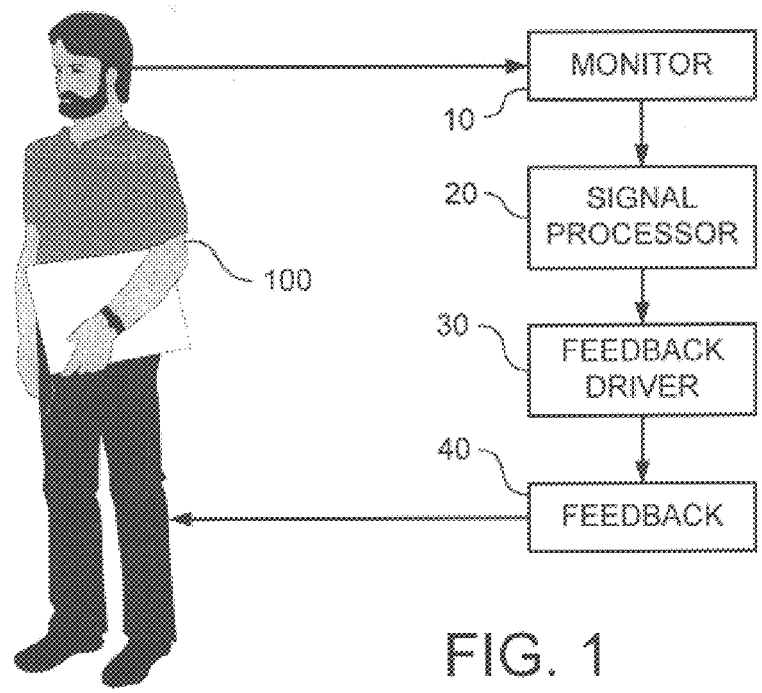
FIG. 1 illustrates a block diagram of an apparatus according to a first embodiment of the present invention in relationship to a subject to be monitored.

The present invention is preferably embodied as a portable device that processes raw EEG in real time and transmits an alarm signal to the subject when an impending sleep state is detected. The alarm signal is transmitted to the subject as auditory, tactile (i.e., vibrational), visual, or electrical stimulus. The alarm signal is optionally transmitted remotely via RF, computer, GPS device, network, infrared (IR), or other means. This portable device prevents the inadvertent onset of sleep by energizing an alarm and awakening the subject when sleep is detected. Optionally, the portable device is empowered to automatically disengage machinery or automatically engage safety processes.

Because the devices embodied according to the present invention are portable, they may be worn on the subject's person or mounted in the cabin of a vehicle being driven by the subject. Contact leads mounted on the subject enable recording of raw EEG data. The devices may be interchanged between plural vehicles. Another optional feature of the portable device is a transmitter to alert other remote devices via wireless communications.

When sleep onset was detected, the subject is awakened by an alert mechanism. The alert mechanism may be auditory, vibrational, electrical, light, RF, global positioning system (GPS) device, via a network, or some combination of the foregoing.

According to the process aspect of the present invention, processed EEG and/or EMG signals are obtained via a disposable or permanent attachment to the individual of an EEG and/or EMG processor. The processed signals are further processed to provide a clear numerical indication of sleep. A device that produces such a clear numerical indication of sleep is available in the form of a wakefulness index monitor (e.g., the Bispectral Index® model A-2000, available from Aspect Medical Systems, Inc. of Natick, Mass.). A wakefulness index monitor translates a subject's EEG waves from the brain into a single number that depicts the alertness level of the brain, with a full scale reading of 100 corresponding a fully awake state and a reading of 0 corresponding to an absence of any brain activity.

Wakefulness index monitors have been strictly used for monitoring of the level of sedation as an indicator of anesthesia effectiveness during surgery. Index levels between 50 and 60 are considered appropriate levels of sedation during surgery. If the index reading on the monitor begins to rise above this range the anesthesiologist is alerted to compensate to prevent the patient's premature awakening.

The present invention uses a wakefulness index monitor to effect the exact opposite result of this prior art usage. Rather than keeping a subject asleep (the prior art goal), the present invention aims to keep the subject awake. This is done by making an analysis of the wakefulness index reading that is output by the wakefulness index monitor.

Although there is some variability from one person to another, wakefulness index readings in the 90's generally indicate a subject who is awake to one degree or another. A high reading like 95 could be characterized as "wide awake" for most persons. But the present invention solves the problem of determining reliably when a given subject is sliding from that wakeful range into the upper edge of sleep.

As a person tires, the value of their wakefulness index begins to drop. Empirical observation has also determined that as a person tires and begins to make the transition from wakefulness into drowsiness their wakefulness index reading begins to oscillate back and forth between two discrete levels. The precise value of these two levels varies somewhat from one individual to another. However, the oscillating pattern where the index value begins to dip and rise is a very consistent characteristic for virtually all people. The number of dips per unit time starts out at a low rate and increases as drowsiness increases.

Thus, the algorithm for detecting impending sleep is based on monitoring not only the absolute bispectral reading value, but also the time at that level, as well as the number of back-and-forth transitions across a predetermined time period.

An alarm setting that is adjustable (e.g., a threshold number of transitions per unit time, or threshold time spent at the lower wakefulness index value, or attainment of an absolute low wakefulness index value), either automatically or with operator intervention, is used as a comparison reference for the numerical indication. The alarm setting is adjusted so as to reliably spot the changes from awake to near sleep to sleep prior to loss of muscular control and prior to loss of sufficient alertness to reliably operate dangerous machinery or computer equipment. When an alarm condition occurs, it is optionally coupled to the machinery in question, public safety equipment, a cell phone, a vibrating alert, ear phones, lights, electrical shocks, computer connection (i.e., network), GPS unit, etc. This stimulus alerts the near asleep person to become aroused. This alert also alerts others to the near sleep state and trigger appropriate actions in a timely fashion. Appropriate actions include to disengage the machinery, to arouse the individual, and/or to take public safety or to take human resource actions that aim to protect the public and/or the individual.

A process according to the present invention may be implemented via a small portable or non-portable, permanently installed, or removable set of devices. Preferably, the device is unaffected or shielded in such a way as to be unaffected by noise, bright lights, extraneous electrical and other stimuli to maintain arousal or an awake state and prevent detriment to the public safety from lack of arousal.

Referring to FIG. 1, a block diagram of an apparatus according to a first embodiment of the present invention is illustrated. A subject 100 to be monitored is connected to a monitor 10 via conventional electrodes (not shown) that couple physiological signals to a physiologic signal processor 20. Preferably, the physiologic signal processor 20 encompasses and EEG processor, an EMG processor, or both. The processed signals produced by the physiologic signal processor 20 are presented as a numerical value to the feedback driver 30. The feedback driver 30 compares the numerical value with an adjustable alarm threshold, based on the comparison selectively indicates an alarm state.

When an alarm state is indicated, the feedback driver 30 causes the feedback transducer section 40 to provide alert signals directly to the subject 100. Preferably the alert signals include audible signals, however, other types of signals are useful for the purpose of preventing the subject 100 from continuing to drift off to sleep.

Figure 2:
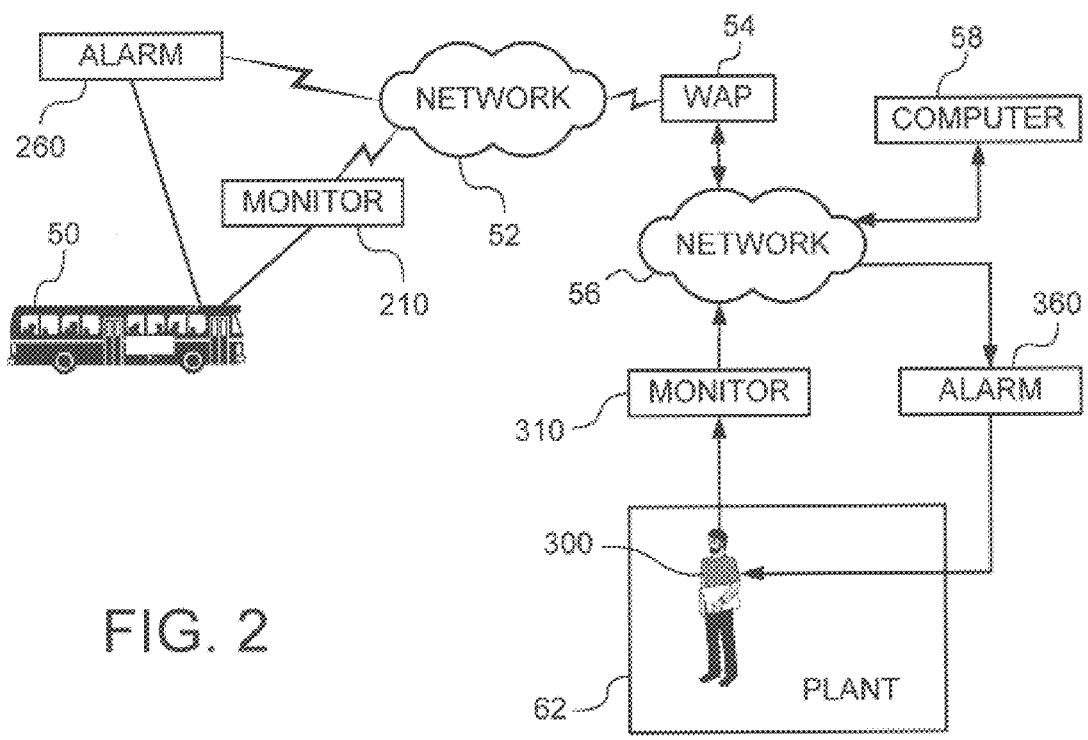
FIG. 2 illustrates a block diagram of apparatus to implement alternate wired and wireless embodiments according to the present invention.

Referring to FIG. 2, a conceptual block diagram of apparatus to implement alternate wired and wireless embodiments according to the present invention is illustrated. When operating in a wireless mode and with central monitoring, a vehicle 50 being operated by an individual wearing a monitor 210 according to the present invention detects the EEG of the driver. That information, which is constantly monitored, is transmitted over a wireless network 52, such as a cellular network. This network 52 may be, for example, and without limitation, an analog network, digital network, or wireless local loop network. When used in a cellular mode, the signal goes from the wireless network through a wireless application protocol (WAP) gateway 54 and over a second network 56. The second network is preferably chosen to be a global interconnected network of networks, such as the Internet. The signal is then directed to an analysis computer 58 for constant monitoring of the signal. When an impending sleep state is detected, the analysis computer 58 sends a signal over the network 56, via the WAP gateway 54, and over the wireless network 52 to the alarm 260 in the vehicle 50 being driven. The alarm 260 then alerts the driver than an impending sleep state exists via an appropriate one of the method discussed above.

In a fixed facility environment, a worker 300 at a plant 62 is monitored by monitors 310. Information from the monitors 310 is sent over the network 56. According to this alternate embodiment, the network 56 may be selected from among an intranet, the Internet, or another network that is suitable under the particular conditions of the plant 62. The signal from the monitor is received at the analysis computer 58, which analyzes the signal for an impending sleep state. If one is detected, a signal is sent over the network 56 to the alarm 360 to alert the plant worker 300 of the impending sleep state.

It will be apparent to those skilled in the art that these architectures are not meant as a limitation. For example, other networks such as those used in aviation are also considered to be within the scope of the present invention.

WORKING EXAMPLE

A wakefulness index monitor of anesthetic depth was modified to serve as a monitor of sleep onset. Fourteen volunteer subjects were monitored for sleep onset. Three methods were used simultaneously to monitor for sleep onset. The first method was to monitor the point at which the volunteer no longer responded to an audio stimulus. The second method was to monitor when perception of sleep was reported. The third method was to monitor the EEG monitor. For all fourteen volunteers, the EEG monitor was able to detect sleep onset (defined by subject self-description on subsequent questioning or inability to respond to an audio stimulus). The modified EEG monitor was further connected to a cell phone dialer with an ear alarm. This alarm arrangement was able to reliably awaken such subjects, and was able to be shielded and derived such that bright lights, etc. did not affect the process.

The value of this device is to prevent operators of dangerous equipment who must function continuously under conditions of fatigue and sleep deprivation from inadvertently falling asleep, or from endangering others. Such operators include airline pilots, commercial ship captains, military personnel, nuclear power plant operators, truck drivers and anesthesiologist, etc. Detection of sleep onset would be transmitted back to the operator to awaken him/her, or could be transmitted to a central facility for evaluation and decision-making, or automatic actions designed to protect individuals or groups of people. The ultimate use of this monitor would be to awaken an operator before loss of consciousness from inadvertent sleep onset results in catastrophe.

The present invention has been described in terms of preferred embodiments, however, it will be appreciated that various modifications and improvements may be made to the described embodiments without departing from the scope of the invention. The scope of the present invention is limited only by the appended claims.

What is claimed is:

1. A method of detecting sleep onset and preventing sleep, the method comprising:
    placing a plurality of contact leads on a subject that detect electroencephalogram (EEG) data;
    transmitting the EEG data to a processing device;
    analyzing the EEG data for a sleep onset condition by deriving numerical index values indicative of wakefulness of the subject and assessing at least one of: the number of level transitions of the numerical index values per unit time, and the length of time spent at or below the lower value of a predetermined transition range; and
    alerting the subject when an sleep onset condition is detected.

2. An impending sleep state alarm comprising:
    a wakefulness monitor adapted to receive at least electroencephalogram (EEG) signals of a subject as an input and produce numerical index values as an output indicative of wakefulness of the subject;
    a signal processor connected to receive the output indicative of wakefulness of the subject and programmed to analyze that output to detect onset of sleep; and
    a feedback transducer connected to the signal processor so as to selectively produce an alarm signal to the subject in the event the signal processor detects onset of sleep;
    wherein the signal processor analyzes the output indicative of wakefulness based on the length of time spent at or below the lower value of a predetermined transition range.

3. An impending sleep state alarm comprising:
    a wakefulness monitor adapted to receive at least electroencephalogram (EEG) signals of a subject as an input and produce numerical index values as an output indicative of wakefulness of the subject;
    a signal processor connected to receive the output indicative of wakefulness of the subject and programmed to analyze that output to detect onset of sleep; and
    a feedback transducer connected to the signal processor so as to selectively produce an alarm signal to the subject in the event the signal processor detects onset of sleep;
    wherein the signal processor analyzes the output indicative of wakefulness based on the number of level transitions of the output per unit time.

4. The impending sleep state alarm of claim 3, wherein the output indicative of wakefulness of the subject comprises a wakefulness index derived at least from EEG signals to provide a single number that depicts the alertness level of the brain.

5. The impending sleep state alarm of claim 3, wherein the wakefulness monitor receives both EEG and electromyelogram (EMG) signals upon which the output numerical index values are based.

6. The impending sleep state alarm of claim 3, wherein the signal processor also analyzes the output indicative of wakefulness based on attainment of a predetermined absolute threshold value.

7. The impending sleep state alarm of claim 3, wherein the feedback transducer provides an auditory stimulus to the subject.

8. The impending sleep state alarm of claim 3, wherein the feedback transducer provides a tactile stimulus to the subject.

9. The impending sleep state alarm of claim 3, wherein the feedback transducer provides a visual stimulus to the subject.

10. The impending sleep state alarm of claim 3, wherein the feedback transducer provides an electrical stimulus to the subject.

11. The impending sleep state alarm of claim 3, further comprising:
a transmitter connected to selectively produce an alarm signal to a remote location in the event the signal processor detects onset of sleep.

12. The impending sleep state alarm of claim 11, wherein the transmitter is selected from the group consisting of: an RF transmitter, a computer, a GPS device, a network, and an infrared transmitter.

13. An impending sleep state alarm comprising:
a wakefulness index monitor adapted to receive electroencephalogram (EEG) and electromyelogram (EMG) signals of a subject as an input and produce numerical index values as an output indicative of wakefulness of the subject;
a signal processor connected to receive the output indicative of wakefulness of the subject and programmed to analyze that output to detect onset of sleep; and
a feedback transducer connected to the signal processor so as to selectively produce an alarm signal to the subject in the event the signal processor detects onset of sleep;
wherein the wakefulness index monitor and the feedback transducer are adapted to be located adjacent the subject and the signal processor is located remotely from the subject;
wherein the signal processor is connected to receive the output indicative of wakefulness of the subject via a network, and the feedback transducer is connected to the signal processor via the network; and
wherein the signal processor analyzes the output indicative of wakefulness based on the number of oscillatory level transitions of the output per unit time.

14. The impeding sleep state alarm of claim 13, wherein the signal processor also analyzes the output indicative of wakefulness based on attainment of a predetermined absolute threshold value.

15. An impending sleep state alarm comprising:
a wakefulness index monitor adapted to receive electroencephalogram (EEG) and electromyelogram (EMG) signals of a subject as an input and produce numerical index values as an output indicative of wakefulness of the subject;
a signal processor connected to receive the output indicative of wakefulness of the subject and programmed to analyze that output to detect onset of sleep; and
a feedback transducer connected to the signal processor so as to selectively produce an alarm signal to the subject in the event the signal processor detects onset of sleep;
wherein the wakefulness index monitor and the feedback transducer are adapted to be located adjacent the subject and the signal processor is located remotely from the subject;
wherein the signal processor is connected to receive the output indicative of wakefulness of the subject via a network, and the feedback transducer is connected to the signal processor via the network; and
wherein the signal processor analyzes the output indicative of wakefulness based on the length of time spent at or below the lower value of a predetermined transition range.

16. An impending sleep state alarm comprising:
a wakefulness monitor adapted to receive at least electroencephalogram (EEG) signals of a subject as an input and produce numerical index values as an output indicative of wakefulness of the subject;
a signal processor connected to receive the output indicative of wakefulness of the subject and programmed to analyze that output to detect onset of sleep; and
a feedback transducer connected to the signal processor so as to selectively produce an alarm signal to the subject in the event the signal processor detects onset of sleep;
wherein the wakefulness monitor and the feedback transducer are adapted to be located adjacent the subject and the signal processor is located remotely from the subject; and
wherein the signal processor comprises a general purpose computer implementing an algorithm for analysis of the output indicative of wakefulness of the subject based on the number of level transitions of the output per unit time.

17. The impending sleep state alarm of claim 16, wherein the signal processor comprises a general purpose computer implementing an algorithm for analysis of the output indicative of wakefulness of the subject based on attainment of a predetermined absolute threshold value.

18. The impending sleep state alarm of claim 16, wherein the signal processor is connected to receive the output indicative of wakefulness of the subject via a network.

19. The impending sleep state alarm of claim 18, wherein the network is a wireless network.

20. The impending sleep state alarm of claim 16, wherein the feedback transducer is connected to the signal processor via a network.

21. The impending sleep state alarm of claim 20, wherein the network is a wireless network.

22. An impending sleep state alarm comprising:
a wakefulness monitor adapted to receive at least electroencephalogram (EEG) signals of a subject as an input and produce numerical index values as an output indicative of wakefulness of the subject;
a signal processor connected to receive the output indicative of wakefulness of the subject and programmed to analyze that output to detect onset of sleep; and
a feedback transducer connected to the signal processor so as to selectively produce an alarm signal to the subject in the event the signal processor detects onset of sleep;
wherein the wakefulness monitor and the feedback transducer are adapted to be located adjacent the subject and the signal processor is located remotely from the subject; and
wherein the signal processor comprises a general purpose computer implementing an algorithm for analysis of the output indicative of wakefulness of the subject based on the length of time spent at or below the lower value of a predetermined transition range.

* * * * *